United States Patent [19]
Palmer et al.

[11] Patent Number: 5,323,902
[45] Date of Patent: Jun. 28, 1994

[54] SAFETY DEVICE FOR HOLDING AND RETAINING HYPOSYRINGES AND THE LIKE

[75] Inventors: Harold J. Palmer, Wyckoff, N.J.; Robert H. Laauwe, Tuxedo, N.Y.

[73] Assignee: Scientific Concepts, Inc., Wyckoff, N.J.

[21] Appl. No.: 132,050

[22] Filed: Oct. 5, 1993

[51] Int. Cl.⁵ ............................................... B65D 85/24
[52] U.S. Cl. .................................... 206/366; 220/212; 220/908
[58] Field of Search ................ 206/365, 366, 210, 364, 206/370; 220/212, 375, 908, 910, 278; 229/907; 215/231, 354

[56] References Cited

U.S. PATENT DOCUMENTS

| | | | |
|---|---|---|---|
| 3,931,905 | 1/1976 | Shumway et al. | 220/278 |
| 4,600,112 | 7/1986 | Shillington et al. | 206/366 X |
| 4,816,307 | 3/1989 | Honeycutt | 206/366 X |
| 5,080,251 | 1/1992 | Noack | 206/366 X |

*Primary Examiner*—Jacob K. Ackun, Jr.
*Attorney, Agent, or Firm*—W. Patrick Quast

[57] ABSTRACT

A safety device for disposing of used hyposyringes employed by home health care professionals is described. A closure assembly permits discarding hyposyringes safely into a container without the danger of hand contact with contaminated surfaces of the safety device, even for objects stuck within the opening to the safety container. A liquid tight seal and liquid absorbent provides additional protection for the home health care professional during the transportation of the safety device after use. The overall design of the assembly permits one hand operation of the assembly.

18 Claims, 4 Drawing Sheets

SAFETY DEVICE FOR HOLDING AND RETAINING HYPOSYRINGES AND THE LIKE

BACKGROUND OF THE INVENTION

This invention relates to a safety device for holding and retaining used hyposyringes, needles, razor blades, and other objects that can constitute a danger to personnel engaged in health related activities.

Hyposyringes and other sharp objects commonly employed by health professionals constitute a potential danger once they have been used. Needles used to deliver medication to a patient, or to draw blood, having an infectious disease can accidentally puncture the skin of a doctor or nurse, causing at a minimum a great deal of anxiety. Obviously, in this current time with the deadly disease called "AIDS", safe disposal of sharp objects used in the routine treatment of patients has become a vital necessity.

Attempts have been made to solve this problem as is evident from U.S. Pat. No. 4,454,944, issued Jun. 19, 1984. This patent teaches the use of a container having a means for passing hyposyringes and the like into an opening in the container. This opening contains pie-shaped flaps which deform downward to permit entry of the hyposyringe, but restrict efforts by children and unauthorized personnel from using their hands to retrieve these objects from the container. Additionally, a locking member permits anchoring the container in one place, as, for example, to a hospital wall.

Another attempt is described in U.S. Pat. No. 4,494,652, issued Jan. 22, 1985. This invention discloses the use of a second container within a first container. An opening in the first container is equipped with deformable pie-shaped flaps so that hyposyringes can be forced between the flaps and thereby gain entrance to the interior of the first container, and thence into the interior of the second container. This second container has an attached cap for securing the opening in this second container, providing additional difficulties for unauthorized personnel to retrieve objects from this second container. In addition, this invention provides a locking device in the first container closure for aiding in the removal of needles from the end of hyposyringes.

U.S. Pat. No. 4,520,926, issued Jun. 4, 1985 addresses the problem of securing hyposyringes and the like being held within a safety container. After dangerous items have been deposited in the container a captive closure is employed to permanently seal the contents within the safety container. This problem is also addressed in U.S. Pat. No. 4,600,112, issued Jul. 15, 1986. This patent teaches the use of an opening to a safety hyposyringe disposal container having a plurality of generally triangular flaps forming a cone shape into the container so that hyposyringes may be placed within the container but not withdrawn. Additionally a permanent cap closure for this opening is threaded to the opening in a manner to prevent accidental permanent sealing of the safety container.

While the above described solutions to the safety disposal problem inherent in the use of hyposyringes and the like have proven generally useful, additional conveniences and precautions are desirable. Today it is estimated that upwards of 300,000 visiting nurses provide a wide variety of in home services. These nurses typically carry with them a supply of hyposyringes, and necessarily some means to dispose of these hyposyringes. These safety disposal devices are often contaminated with bodily fluids containing potentially deadly pathogens. It is therefore important to provide health professionals with economical, convenient, portable, and liquid leak proof safety disposal devices that provide them with as much protection against accidental needle sticks and infection as can be reasonably done in these circumstances.

Therefore it is a primary object of the invention to provide a safety device for holding and retaining used hyposyringes and the like for the protection of the user against accidental infections.

An additional object of the invention is to provide for positive pressure displacement of items into the safety device without the necessity for the hands of the health professional coming in contact with potentially contaminated portions of the safety device.

A further object of the invention is to provide a safety device for hyposyringes and the like that resists puncture by needles and other sharp objects.

Still another object of the invention is to provide a liquid tight, leak proof safety device for the disposal of hyposyringes and the like.

An additional object of the invention is to provide an economical to manufacture safety device for hyposyringes and the like disposal.

A further object of the invention is to provide a safety device for hyposyringe and the like disposal that is portable, and that can be conveniently carried about during normal routines by health professionals.

Yet another object of the invention is to provide an assembly which permits one hand operation.

SUMMARY

These and other objects are obtained by the instant invention of a safety device for the disposal of hyposyringes and the like. A health professional, such as a home health care nurse, typically visits a number of patients each day. The nurse carries a variety of medicinals and means for dispensing them in a carrying case. The instant invention envisions a system for carrying sterile, unused hyposyringes in green colored containers, with other red colored containers having a special closure. These red colored containers, together with their closures, would serve as a safety device for disposing of used hyposyringes with little or no danger of accidental infectious contamination of the health care professional. The day to day activities of the nurse operating outside of a hospital environment virtually demands an economical, easily portable and easy to use disposal system for hyposyringes and the liquids that can contaminate the syringes.

In the instant invention an elongated container with a solid base and an open top is fabricated out of a plastic material such as polyethylene or polyvinylchloride (PVC). The neck of the container is formed so that an insert will snap fit over the top open end of the container. To absorb liquids that gain access to the interior of the container, corn starch or another suitable moisture absorbent material is placed in the base of the container. Indents are formed in the sides of the container a spaced distance above the base of the container so that a metal plate, such as an aluminum plate, can snap fit into the base portion of the container immediately below the indents. The purpose of this metal plate is to prevent hyposyringe needles from piercing the base of the container and thus posing a potential danger for the nurse. Alternatively the material for this plate can be plastic, or the container itself can be fabricated with a base portion sufficiently strong to resist puncture by a needle.

A version of the closure for the container envisions a two piece construction, an inner portion and an outer portion being hingedly connected to each other. The inner portion is designed to substantially cover the opening at the top of the container except for an area approximately $\frac{1}{2}"$ in diameter at the center of the annular opening to the container. This inner portion has a groove at its periphery so that this component of the closure can snap fit over the lip of the container opening. Generally triangular shaped fins or flaps extend from the periphery of this inner portion of the closure, projecting downward into the container, forming a cone shape within the container. At the end of four fins terminating at the cone opening is a downwardly projecting additional portion of these fins, each of said portions being spaced approximately 90 degrees apart, and being generally parallel to the side walls of the container. The purpose of these additional fin projections is to help prevent hyposyringes from wedging in this opening, especially smaller ones, as, for example, one ounce hyposyringes. This inner portion of the closure can be fabricated from rubber, plastic materials, or even metal.

To assemble the complete safety device the inner portion of the closure snap fits over the edge of the container opening. The solid, outer portion of the closure then is hingedly connected to the inner portion of the closure by means of two knob like projections on the outer portion which snap fit into two matching holes located in two projections on the inner portion of the closure, forming a secure hinge connection between the outer and inner portions. Once this hinge connection is in place the solid outer portion of the closure assembly snaps shut over the top surface of the inner portion of the closure assembly. A tubular protrusion with a solid base is formed into the center of the solid, outer portion of the closure so that as this solid plastic cap is snapped into place, this protrusion extends through the $\frac{1}{2}"$ opening at the apex of the cone of the inner portion of the closure. A convenient lift lip on the periphery of this solid, hinged cap portion of the closure provides for easily grasping the cap with the hand of the operator for closing and opening this outer cap as desired.

In this manner an economical and easily transported safety device is provided for field work by a variety of health care providers. Hyposyringes are disposed of safely without the necessity for the health care provider to touch potentially contaminated fins since the protrusion at the center of the outer solid cap portion automatically forces even stuck needles and the like into the container when this outer portion is secured to the inner portion of the closure. Additional safety is provided by the liquid leak proof nature of the closure assembly and container, and the liquid absorbent within the container, even when the safety device is carried about in a horizontal position.

DETAILED DESCRIPTION

Figure 1:
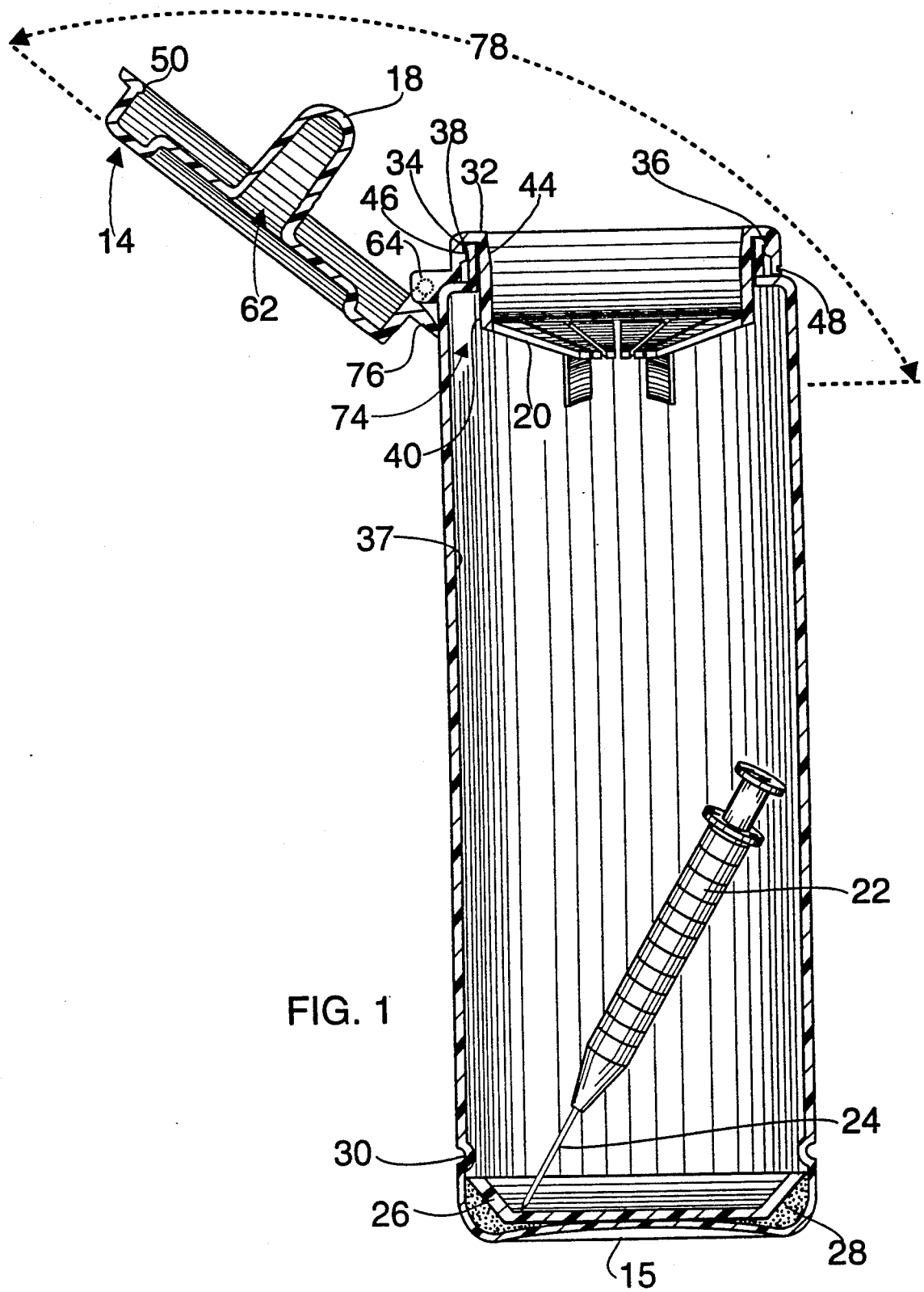
FIG. 1 is a perspective sectional view of one version of the safety device of the invention, showing the outer portion of the closure assembly in open position.
Figure 2:
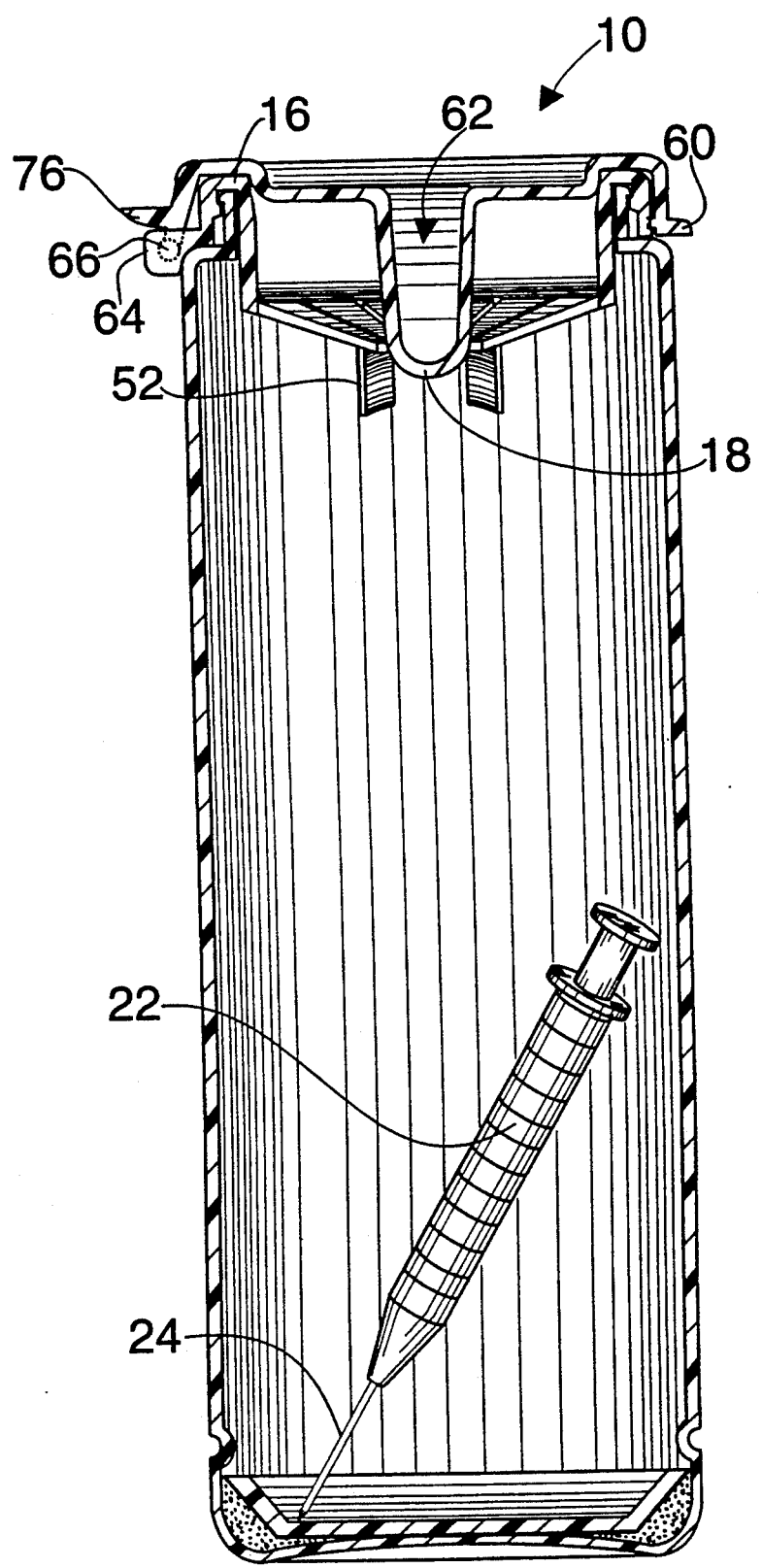
FIG. 2 is a side, elevation sectional view of one version of the safety device of the invention, with the container closure assembly in place on the container.
Figure 3:
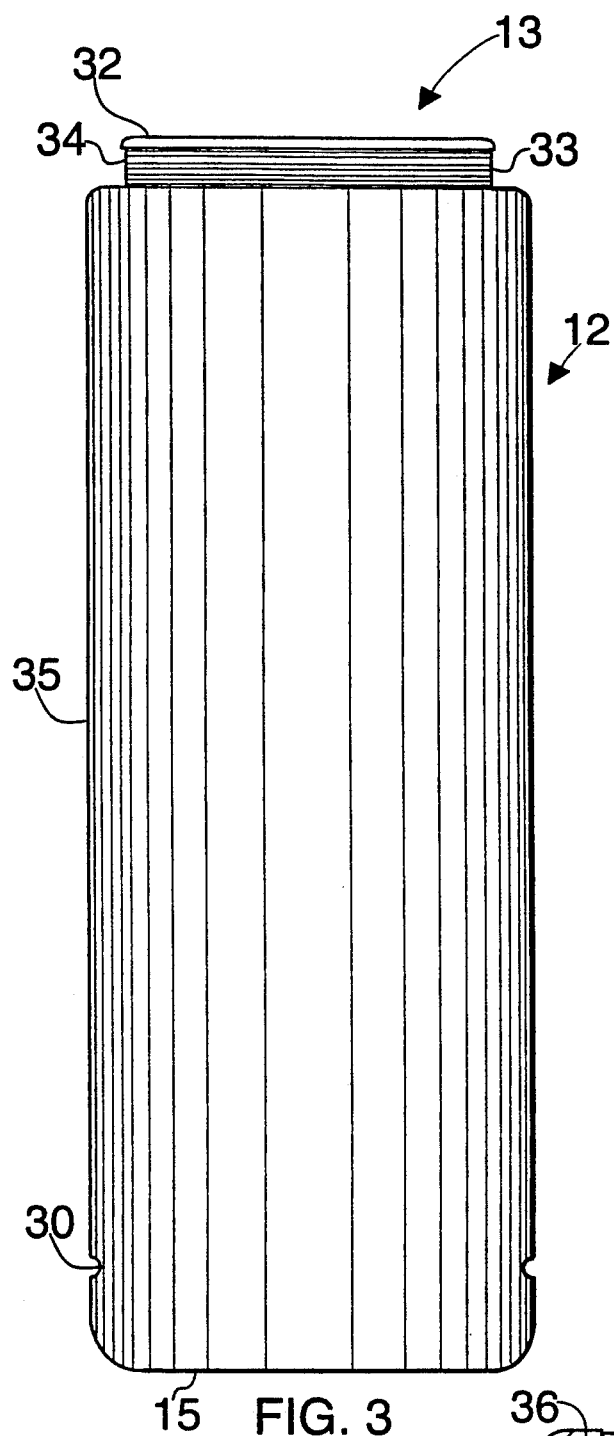
FIG. 3 is a perspective view of one version of the container portion of the safety device of the invention.

Referring now to FIGS. 1-3 a complete safety device 10 for holding and retaining hyposyringes 22 and the like, including the liquids that may contaminate these syringes, is shown. The device consists primarily of a container 12 having a solid base 15 and an open top 13 (FIG. 3), and a closure assembly for the opening 13 consisting of an inner portion 16 and an outer portion 14. The container 12 can be made out of metal, but for economical manufacture a suitable plastic material such as polyethylene or polyvinylchloride (PVC) would be preferable. The plastic can be clear for viewing the interior of the container although this is not necessary for the proper functioning of the invention. Typical dimensions for the container would be approximately $7\frac{1}{4}"$ in length by approximately $2\frac{1}{4}"$ in diameter.

The closure assembly for the container opening 13 consists essentially of an inner portion 16 and an outer portion 14, which provides for safe one way disposal of hyposyringes while maintaining a liquid tight seal, as will be more fully explained. To place the closure assembly on the container 12 opening, the inner portion 16 (FIG. 4) of the closure assembly snap fits over the lip of the container opening 13. The solid, outer portion 14 of the closure assembly is hingedly connected to the inner portion. At this point objects such as hyposyringes 22, together with their needles 24 can be safely discarded by slipping them through the opening 58 (FIG. 4) in this inner closure member. The flexible, slotted fins 20 structure of the inner closure portion 16 form a cone shape which has an opening at the apex of the cone to permit the entry of objects being pressed into the interior of the container. The memory of the fins then returns the fins to their original position when pressure is released. In this manner objects gain entrance to the interior of the container but can only be removed from the container with great difficulty. A plurality of downwardly projecting additional portion 52 of the fins at the apex of said cone provide an additional means for preventing hyposyringes, particularly small hyposyringes such as one ounce hyposyringes, from becoming wedged in the opening.

In the base of the container, a metal plate 26 (FIG. 2), situated beneath an annular indent 30 in the wall 35 of the container protects against accidental puncture of the container wall. This plate can be made of steel or aluminum, or even a tough plastic material. Alternatively the container 12 can be fabricated out of puncture proof materials.

For additional security against the movement of liquids within container, an absorbent powder 28 such as corn starch, or an absorbent material can be placed in the base portion of the container.

Finally, to secure the safety device in a liquid leak proof manner the solid, outer portion 14 of the closure assembly, which is hingedly connected to the inner portion 16 of the closure assembly, is pressed to snap fit over the areas of inner portion 16 of the closure assembly that are outside of the container. By making this closure the protrusion 18 at the center of the outer portion 14 is caused to pass through the opening 58 in the inner portion 16 of the closure assembly, necessarily pushing any objects such as, for example, a hyposyringe 22, into the interior of the container. It is important to note that this action of the "hypodermic syringe barrel" shaped protrusion 18 at the center of the outer portion 14 of the closure assembly in forcing objects into the interior of the container 12 does so without any possibility of the hands (not shown) of a health professional coming in contact with any potentially contaminated surfaces of the inner portion 16 of the closure assembly. A lift lip 60 is built-into the periphery of the outer portion to simplify opening or closing access to the opening 58 in the inner portion of the closure assembly.

The safety device can be opened and closed with one hand. As can best be seen in FIG. 2, if the container is placed on a horizontal supporting surface, such as a table top (not shown), the operator can open the safety device with one hand (not shown) by simply encircling the container with the palm and fingers of the hand and then lifting the lift lip with the thumb. Similarly the safety device can be closed with one hand by simply flipping the outer portion 14 of the closure assembly over the inner portion 16, and then snapping the projection 50 on the lift lip 60 into slot 48 on the inner portion 16. A projection 76 (FIG. 1) adjacent the hinge connection of the outer portion of the closure assembly prevents the outer portion 14 from defining an angle 78 greater than approximately 130 degrees in the fully open position of the outer portion in comparison to the fully closed position of the outer portion. In this manner the center of gravity of the complete safety device is not altered to such an extent as to make the container and closure assembly unstable, and prone to toppling over, when the outer portion is opened to gain access to the interior of the container.

Figure 4:
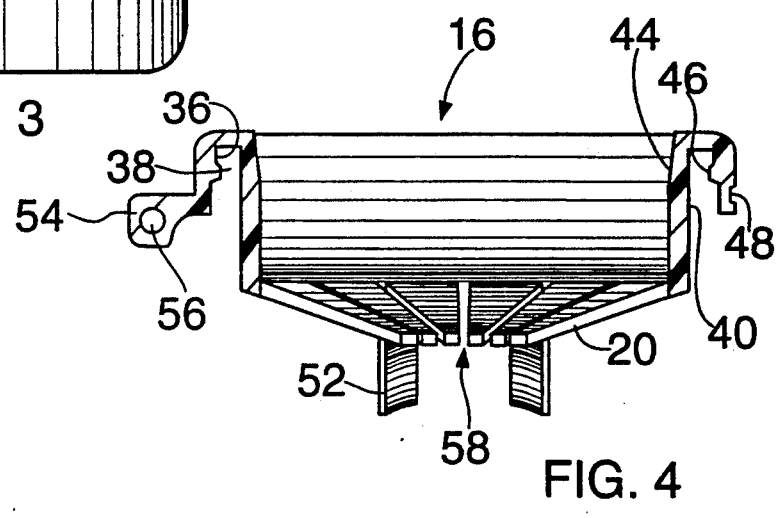
FIG. 4 is the inner portion of the closure assembly for the container of the safety device illustrating the cone shape formed by the fins of this portion of the closure assembly.
Figure 5:
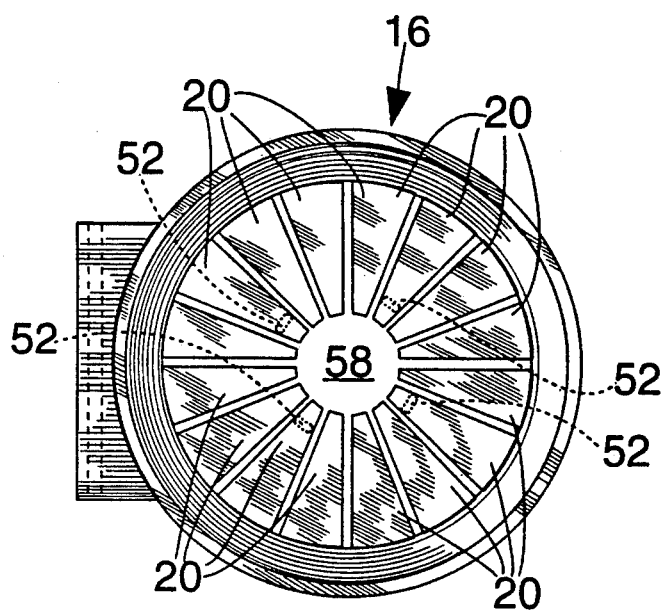
FIG. 5 is a top plan view of the inner portion of the closure assembly for the container of the safety device as shown in FIG. 3.

FIGS. 4 and 5 illustrate in detail one version of the inner portion 16 of the closure assembly of the invention. A generally rectangularly shaped channel 38 at the periphery of the inner portion 16 snap fits over the planar surface 32 on the lip of the opening of the container (FIG. 3). The outer wall 36 of this channel contacts the outer wall 33 of the lip of the container, and the channel 38 inner wall 40 contacts the inner wall 42 (FIG. 2) of the container extending from the lip downwardly opposite the external wall of the container lip 33 and the annular indent 34 between the wall of the lip 33 and the remainder of the tubular body 35 of the container. This tight fit between the opening of the container and walls 36 and 40 of the inner closure acts to provide a reliable, liquid tight seal, holding liquids in the container even when the container is held in a horizontal position. By having the inner wall 40 of the inner closure portion of the closure assembly a spaced distance away from the inner wall 37 (FIG. 2) of the container 12 as this wall extends downward into the container, a reservoir area 74 (FIG. 1) for liquids in this portion of the container is created. This is important when the container is held in a horizontal position, and liquids within the container are not sequestered by a moisture absorber. Additionally, an indent 46 runs the complete circumference of the generally circular in shape inner portion 16 within generally rectangular shaped channel 38, and makes contact with the outer wall 34 of the annular indented portion of the container.

The circular shaped inner portion has half of the hinge portion for connecting the inner and outer portions of the closure assembly together. This consists of two laterally projecting extensions 54 (FIG. 4) with holes 56 within each of the projections for accepting the second half of the hinge portion, i.e. the knob like projections 66 (FIG. 6) which extend laterally from the periphery of the outer portion 14 on two extending arms 64. Immediately opposite the hinge projections 54 and holes 56 is a slot 48 within the downwardly extending outer surface of the inner portion extending over the lip of the container. The function of this slot is to accept the protrusion 50 on the inner surface of the outer portion so that a positive "feel" for the fully closed position of the outer portion is given when the protrusion 50 snaps into the slot 48.

Immediately adjacent the opening 58 at the apex of the cone within the inner portion of the closure, additional downward extensions 52 of a plurality of the fins provides for guiding hyposyringes, and especially smaller hyposyringes such as one ounce hyposyringes, through the opening 58 in the apex without becoming wedged within the opening. Four such extensions 52 are considered adequate, spaced approximately 90 degrees apart from one another. The inner portion of the closure assembly can be made out of a variety of materials including metal, natural rubber, or plastics including synthetic elastomers. For example, low density polyethylene can be employed to follow the contours of the outer portion of the closure assembly.

Figure 6:
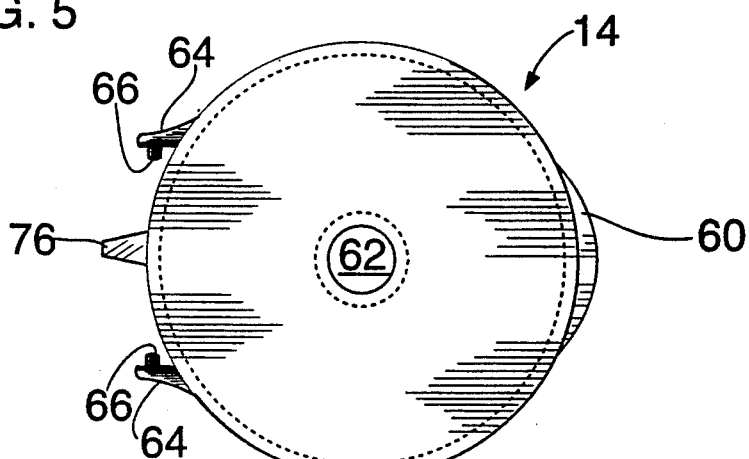
FIG. 6 is a top plan view of the outer portion of the closure assembly.
Figure 7:
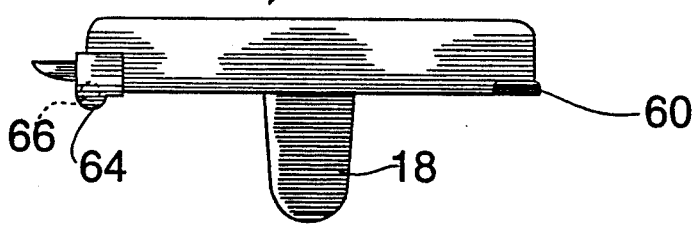
FIG. 7 is a side, elevation view of the outer portion of the closure assembly.
Figure 8:
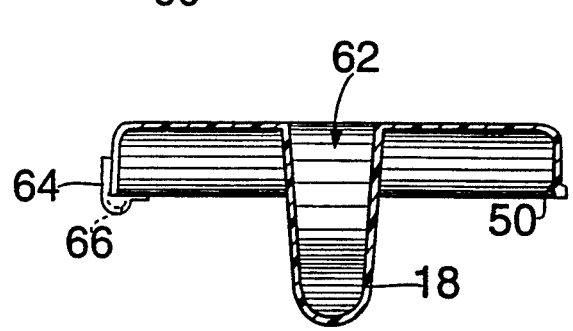
FIG. 8 is a side, elevation sectional view of the outer portion of the closure assembly.

FIGS. 6–8 illustrate in detail one version of the outer portion 14 of the closure assembly. This outer portion can be made out of a variety of materials, the most suitable being plastics such as ABS (acrylonitrile-butadiene-styrene), polypropylene, and high density polyethylene. As can be best seen in FIG. 6 extending laterally from one portion of the generally circular shaped outer portion of the closure assembly are two hinge knob securing arms 64 with two hinge knobs 66 extending perpendicular to and away from the arms. These hinge knobs 66 snap fit into the matching holes 56 within the two laterally projecting extensions on the inner portion 16 of the closure assembly to provide a secure hinge connection between the two closure components. Immediately opposite the hinge knob securing arms is a lift lip 60 extending laterally from the periphery of the outer portion to provide for convenient access to the opening 58 within the inner portion for object disposal, and to seal this opening as required. At the center of the outer portion an opening 62 defines the area for the hypodermic syringe like projection 18. FIG. 8 details the projection 50 on the inner surface of the outer portion immediately adjacent the lift lip for providing a positive "feel" for a secure closure of the outer portion of the closure assembly when the projection 50 snaps into the indent 48 of the outer surface of the inner portion.

To assemble the complete safety device, the opening to the container is partially closed with the inner portion 16 of the closure assembly, and the outer portion 14 of the assembly is hingedly connected to the inner portion as has been described. To fully close the safety device for transportation or eventual disposal the lift lip 60 on the outer portion is grasped by hand (not shown) and secured over the inner portion of the closure assembly. The contour of the inner portion of the assembly where this portion is secured to the lip of the container closure matches the contours of the interior surfaces of the outer portion of the assembly, providing a reliable, friction fit liquid seal. Also, typically chamfered surface 44 co-acts with the mating surface of the outer portion 14 to further enhance the tight liquid seal of the device. In addition the projection 50 and slot 48 feature of the closure assembly provides a positive "feel" for when the safety device is adequately closed.

Thus it can be seen that the safety device of the invention provides a convenient and economical disposal system for hyposyringes and the like, especially for health professionals away from the hospital environment. Hyposyringes are easily disposed of safely, even in the case where needles and other objects become temporarily lodged in the opening to the interior of the container, which, in the case of other disposal devices would normally subject the health professional to potential danger from a contaminated surface in or near this opening when a hand is used to push the lodged object into the interior of the container. Further, an assembly has been described which permits one hand operation of the assembly. Additional safety precautions have been described, especially when transporting the safety device when it is contaminated with potentially infectious liquids.

While the present invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. A system for holding and retaining hyposyringes and sharp instruments, comprising:
    (a) a container for said hyposyringes, said container having a solid base and an opening at the top;
    (b) a closure assembly for said opening;
    (c) said closure assembly comprising in combination, a first member, said first member having means for permitting hyposyringes and the like to be passed through said first member and into said container under the exerted pressure of an operator, said means for permitting said passage of said hyposyringes tending to resist the passage of said hyposyringes when said pressure is released; and
    (d) a second member, said second member being comprised of a solid disc portion, with a centrally located protrusion extending from and being perpendicular to said disc so that when said first member is secured to said opening in said container hyposyringes may be inserted into said container, said means for permitting said passage of said hyposyringes yielding to said exerted pressure of said operator so that said hyposyringes gain access to the interior of said container, said second member then being secured over said first member and said opening in said container, said closure assembly comprising means for providing a liquid tight seal with said opening in said container, said protrusion in said second member dimensioned to extend downward through said first member a spaced distance into the interior of said container and between said means for permitting said passage of said hyposyringes, when said first member is secured over said second member so that any portions of said hyposyringes remaining within said means for permitting said passage of said hyposyringes in said first member are forced into the interior of said container without the necessity for the hands of said operator contacting any surfaces of said first member.

2. The system according to claim 1 wherein said first member is comprised of an annular portion from which a plurality of slotted, flexible fins extend axially and downwardly a spaced distance into the interior of said container, said flexible fins forming a generally cone shape having an opening at the apex of said cone so that under said exerted pressure of said operator said hyposyringes are inserted past said fins and into the interior of said container, said fins then returning to their original non-stressed position when said pressure is released so that said hyposyringes now tend to be retained by said fins when said container is inverted.

3. The system according to claim 2 wherein more than one of said fins have additional portions affixed at the end of said fins immediately adjacent said apex of said cone, said additional portions extending a spaced distance downwardly into the interior of said container, said additional fin portions being generally parallel to the sides of said container, so that said additional portions of said fins act as a guide to said hyposyringes being inserted past said fins to assist in preventing said hyposyringes from becoming wedged in said apex of said cone.

4. The system according to claim 1 wherein said closure assembly comprises means for facilitate separate from said container.

5. The system according to claim 1 wherein said second member of said closure assembly contains means for connecting said second member to said first member so that said solid disc portion of said second member remains in a non-sealing association with said container in a first position.

6. The system according to claim 5 wherein said means for connecting said second member to said first member provides a hinged connection between said second member and said first member.

7. The system according to claim 4 wherein said second member has an integral lift lip at the periphery of said second member.

8. The system according to claim 1 wherein said first member has means for being connected to said container at the opening of said container, forming a liquid tight seal at the juncture of said container and the peripheral portion of said first member when said first member is connected to said container.

9. The system according to claim 8 wherein when said first member is connected to said container, and said second member is connected to said first member and said container, said safety device forms a liquid tight enclosure.

10. The system according to claim 1 wherein said protrusion in said second member is closed at the base portion of said protrusion which extends away from the solid disc portion of said second member.

11. The system according to claim 10 wherein said protrusion is an integral part of said second member.

12. The system according to claim 1 wherein said base of said container is reinforced with a separate needle puncture resisting plate.

13. The system according to claim 1 wherein said base of said container additionally contains an absorbent for sequestering fluids that gain access to the interior of said container.

14. The system according to claim 1 further comprising means for providing said operator with a "feel" for the adequate closing of said second member to said first member when said second member is secured to said first member.

15. The system according to claim 6 further comprising means for enabling said operator to open and close said safety device with one hand, said second member being capable of being opened by said operator only to a predetermined angle, said predetermined angle having been previously determined to be an angle that will not significantly distort the combined center of gravity of said container and said first and second members when said container is placed in a vertical position on a solid, horizontal surface such as a table top, and said safety device is opened with said one hand of said operator, so that said container in said vertical position resists being toppled over due to a different weight distribution acting on said container due to said second member being in said open position.

16. The system according to claim 15 wherein said predetermined angle is a maximum angle of approximately 130 degrees from the position of said second member when said second member is in said closed position.

17. The system according to claim 8 further comprising means for retaining a quantity of liquid within said container in a reservoir area between the inner wall of said first member and the inner wall of said container when said container is placed in a horizontal position.

18. A system as recited in claim 1, further comprising another container, said another container having means for holding unused hyposyringes and sharp instruments, said first container for holding used hyposyringes and sharp instruments, said first container having a first color and said second container having a second color different from said first color.

* * * * *

UNITED STATES PATENT AND TRADEMARK OFFICE
CERTIFICATE OF CORRECTION

PATENT NO. : 5,323,902

DATED : June 28, 1994

INVENTOR(S) : HAROLD J. PALMER and ROBERT H. LAAUWE

It is certified that error appears in the above-identified patent and that said Letters Patent is hereby corrected as shown below:

At column 8, line 34, change the word "for" to --to--.

At column 8, line 34, change the word "separate to --separation--

Signed and Sealed this

Twentieth Day of September, 1994

Attest:

BRUCE LEHMAN

Attesting Officer      Commissioner of Patents and Trademarks